United States Patent [19]

Robinson et al.

[11] Patent Number: 4,880,776

[45] Date of Patent: Nov. 14, 1989

[54] PLASMIN A-CHAIN UROKINASE B-CHAIN HYBRID PROTEIN

[75] Inventors: Jeffery H. Robinson; Ian Dodd, both of Epsom, England

[73] Assignee: Beecham Group p.l.c., United Kingdom

[21] Appl. No.: 173,430

[22] Filed: Mar. 25, 1988

Related U.S. Application Data

[63] Continuation-in-part of Ser. No. 41,710, Apr. 23, 1987, abandoned, and a continuation-in-part of Ser. No. 684,593, Dec. 21, 1984, Pat. No. 4,752,581.

[30] Foreign Application Priority Data

Dec. 24, 1983 [GB] United Kingdom ............... 8334498
Apr. 23, 1986 [GB] United Kingdom ............... 8609948

[51] Int. Cl.$^4$ .................. C12N 9/68; C12N 9/72; A61K 37/54; A61K 37/547
[52] U.S. Cl. .................................. 514/2; 530/363; 530/403; 530/807; 530/811; 435/212; 435/215; 435/217; 424/94.64; 424/94.2
[58] Field of Search ............ 514/2; 530/350, 363, 530/403, 807, 811; 435/177, 217, 215, 212; 525/54.1; 424/94.2, 94.63, 94.64

[56] References Cited

U.S. PATENT DOCUMENTS

| | | | |
|---|---|---|---|
| 4,082,612 | 4/1978 | Robbins et al. | 435/217 |
| 4,285,932 | 8/1981 | Smith . | |
| 4,507,283 | 3/1985 | Smith | 435/217 X |
| 4,545,988 | 10/1985 | Nakayama et al. | 435/217 X |
| 4,600,580 | 7/1986 | Smith | 424/88 X |
| 4,752,581 | 6/1988 | Robinson et al. | 435/217 |

FOREIGN PATENT DOCUMENTS

| | | |
|---|---|---|
| 9879 | 4/1980 | European Pat. Off. . |
| 155387 | 9/1985 | European Pat. Off. . |
| 196920 | 10/1986 | European Pat. Off. . |
| 213794 | 3/1987 | European Pat. Off. . |

OTHER PUBLICATIONS

Summaria et al., J. Biol. Chem., vol. 254, pp. 6811–6814, 1979.
Robbins et al, Biochemistry, vol. 25, pp. 3603–3611, Jun. 1986.
Jackson et al, Biochem., 1982, 21, 6620–6625.
D. Collen et al, Thromb Haemostas (Stuttgart), 52 (1), 24–26, 1984.
Fuchs et al, Blood, vol. 65, No. 3 (Mar.), 1985; pp. 539–544.
Nakayama et al, "The Plasmin Heavy Chain–Urokinase Conjugate: A Specific Thrombolytic Agent", Throm and Haem, 56 (3), 361–370 (1986).
Robbins et al, "Covalent Molecular Weight 292,000 Hybrid Plasminogen Activator Derived From Human Plasmin Amono–Terminal and Urokinase Carboxyl–Terminal Domains", Biochemistry, vol. 25, No. 12, pp. 3603–3611 (1986).
Summaria et al, J. Biol. Chem., 251, No. 18, 5810–5813 (1976).

Primary Examiner—John Kight
Assistant Examiner—Nathan M. Nutter
Attorney, Agent, or Firm—Jacobs & Jacobs

[57] ABSTRACT

A hybrid protein which comprises plasmin A-chain linked to urokinase B-chain, the catalytic site of which is blocked by a removable blocking group.

9 Claims, No Drawings

PLASMIN A-CHAIN UROKINASE B-CHAIN HYBRID PROTEIN

The present application is a continuation-in-part of our copending application Ser. No. 684,593, filed Dec. 21, 1984, which is incorporated herein by reference thereto, now U.S. Pat. No. 4,752,581. The present application is also a continuation-in-part of our copending application Ser. No. 041,710, filed Apr. 23, 1987 and now abandoned, which is incorporated herein by reference thereto.

The present invention relates to novel fibrinolytic enzymes, to processes for their preparation and to their use in treating thrombotic diseases.

Human fibrinolytic enzymes may be divided into two general classes; namely, one class that directly digests fibrin, for example, trypsin and plasmin, and a second class that indirectly digests fibrin by activating the inactive zymogen, plasminogen. The latter class, comprising the plasminogen activators, is represented by two major types based on immunological criteria, molecular weight and polypeptide composition (see Collen, D. et al, 1982, Thromb. Haemostas., 48, 294–296). On major type, the urokinase-type plasminogen activators (u-PA) resemble the urinary enzyme urokinase, whereas the other major type, tissue-type plasminogen activators (t-PA) resemble extrinsic activators found in blood, activators extracted from tissues by chaotropic salts and activators secreted by cultured melanoma cells (see Rijken, D. C. and Collen, D., 1981, J. Biol. Chem., 256, 7035–7041; Rijken, D. C. et al, J. Lab. Clin. Med., 97, 477–478). Human plasminogen activators have been used in the treatment of thrombosis. However, the u-PA have the disadvantage that they activate circulating plasminogen as efficiently as fibrin-bound plasminogen and both the u-PA and also the t-PA have the disadvantage that their activity disappears rapidly in vivo due to rapid clearance and inactivation by natural antiproteases.

The above human fibrinolytic enzymes belong to a class of proteases which exist in both a single chain and a 2-chain structure, the two chains being connected by disulphide bridges. It has been demonstrated that the desirable properties of two proteases may be united by forming a single hybrid protein molecule which includes a chain from each of the two proteases.

The aforementioned U.S. Pat. No. 4,752,581, which corresponds to European Published Application No. EP-0 155 387, discloses fibrinolytically active hybrid protein which comprises one chain of a 2-chain protease linked to a chain of a different 2-chain protease, or to the same chain of the same protease, at least one of the chains in the hybrid protein being derived from a fibrinolytically active protease, such that the hybrid protein has a catalytic site essential for fibrinolytic activity which is optionally blocked by a removable blocking group.

The 2-chain protease structure includes an A-chain which has no protease activity and a B-chain with protease activity.

According to the present invention there is provided a hybrid protein which comprises plasmin A-chain linked to urokinase B-chain, the catalytic site of which is blocked by a removable blocking group.

As used herein the expression 'removable blocking group' includes groups which are removable by hydrolysis at a rate such that the pseudo-first order rate constant for hydrolysis is in the range of $10^{-6}$ sec$^{-1}$ to $10^{-2}$ sec$^{-1}$ in isotonic aqueous media at pH 7.4 at 37° C.

Such blocking groups are described in European Patent No. 0009879 and include acyl groups such as optionally substituted benzoyl or optionally substituted acryloyl.

Suitable optional substituents for benzoyl blocking groups include halogen, $C_{1-6}$ alkyl, $C_{1-6}$ alkoxy, $C_{1-6}$ alkanoyloxy, $C_{1-6}$ alkanoylamino, amino or p-guanidino.

Aryloyl blocking groups may be optionally substituted by $C_{1-6}$ alkyl, furyl, phenyl or $C_{1-6}$ alkylphenyl, or disubstituted by $C_{3-6}$ polymethylene.

Preferably the removable blocking group is 4-aminobenzoyl or cyclohexylideneacetyl (3,3-cyclohexylacryloyl).

The hybrid proteins of the invention may be prepared as described in the aforementioned U.S. Pat. No. 4,752,581 and EP-0 155 387 by mixing plasmin A-chain with optionally blocked urokinase B-chain, optionally with dialysis, under oxidative conditions, followed as necessary by the blocking of the catalytic site on the hybrid protein.

Preferably, the mixing/dialysis process is carried out for a period of one or more days in the presence of molecular oxygen, and the resulting hybrid protein isolated by chromatographic techniques.

There are various methods known in the prior art that might be beneficially employed to increase the rate of disulphide bond formation; for example, employing —SSO$_3$ derivatives as described in the U.K. Patent GB No. 2072680 for synthesis of insulin.

The blocking of the catalytic site on the hybrid protein is achieved by carrying out the blocking on either urokinase B-chain or on the formed hybrid protein by methods analogous to those described in European Patent No. 0009879. The blocking is preferably effected after formation of the hybrid protein.

Alternatively, the hybrid proteins of the invention may be prepared by taking the genetic information (DNA sequence) of each protein, cutting and lighting this to construct a new DNA sequence coating for the hybrid protein, and expressing this DNA in a prokaryote or eukaryote host, followed by blocking of the catalytic site as described above.

The hybrid proteins of this invention are preferably administered as a pharmaceutical composition for the treatment of thrombotic diseases.

Accordingly the present invention also provides a pharmaceutical composition comprising a hybrid protein of the invention in combination with a pharmaceutically acceptable carrier.

The compositions according to the invention may be formulated in accordance with routine procedures as pharmaceutical compositions adapted for intravenous administration to human beings.

Typically compositions for intravenous administration are solutions of the sterile hybrid protein in sterile isotonic aqueous buffer. Where necessary the composition may also include a solubilising agent to keep the hybrid protein in solution and a local anaesthetic such as lignocaine to ease pain at the site of injection. Generally, the hybrid protein will be supplied in unit dosage form for example as a dry powder or water free concentrate in a hermetically sealed container such as an ampoule or sachette indicating the quantity of protein in activity units, as well as an indication of the time within which the free protein will be liberated. Where the protein is to be administered by infusion, it will be dispensed with an infusion bottle containing sterile pharmaceutical grade 'Water for Injection'. Where the protein is to be administered by injection, it is dispensed with an ampoule of sterile water for injection. The injectable or infusable composition will be made up by mixing the ingredients prior to administration.

The quantity of material administered will depend upon the amount of fibrinolysis required and the speed with which it is required, the seriousness of the thromboembolic condition and position and size of the clot. The precise dose to be employed and mode of administration must per force in view of the nature of the complaint be decided according to the circumstances by the physician supervising treatment. However, in general, a patient being treated for a mature, fresh or nascent thrombus will generally receive a daily dose of from 0.01 to 10 mg/kg of body weight either by injection in up to five doses or by infusion.

Within the above described dosage range, no adverse toxicological effects are indicated with the compounds of the invention.

Accordingly, in a further aspect of the invention there is provided a method of treating thrombotic diseases, which comprises administering to the sufferer an effective non-toxic amount of a hybrid protein of the invention.

The invention also provides a hybrid protein of the invention for use as an active therapeutic substance and, in particular, for use in the treatment of thrombotic diseases.

The following Examples illustrate the invention.

EXAMPLE 1

Synthesis of 4aminobenzoyl (lys$_{77}$ plasmin A-chain) ile$_{159}$ u-PA (AB→u-PA hybrid) and 4-aminobenzoyl u-PA (AB→u-PA)

Purified lys$_{77}$ plasmin A-chain/ile$_{159}$ u-PA (800 μl, 152 μg/ml), prepared as described in Example 3 of the aforementioned U.S. Pat. No. 4,752,581 in phosphate-buffered saline (Dulbecco 'A', Oxoid; PBS 'A'), 0.01% Tween 80, pH 7.3 was mixed with 0.25M L-lysine, 0.55M D-mannitol, 0.01M ε-aminocaproic acid (80 μl). 4-aminobenzoic acid p-amidinophenyl ester.HCl (EP-A-O 091 240 Example 1(b)) (110 μM, 40 μl) was added to the mixture and incubated at 25° C. for 35 min. The solution was then buffer-exchanged into PBS 'A', 0.01% Tween 80 2.0 ml) using Sephadex G25 (PD10, Pharmacia), aliquoted and stored at −70° C.

A deacylation study carried out on a thawed aliquot in PBS 'A', 0.01% Tween 80 at 37° C. gave a deacylation rate constant of $4.4 \times 10^{-5}$ sec$^{-1}$. This study also demonstrated that at least 94 percent of the AB→u-PA hybrid was in the acyl form prior to deacylation.

4-aminobenzoyl u-PA was synthesised by a similar method to the one described above for AB→u-PA hybrid. The u-PA was 98% acylated and had a deacylation rate constant of $1.02 \times 10^{-4}$ sec$^{-1}$ in 0.05M phosphate, 0.1M NaCl, 0.01% Tween 80, pH 7.4 at 37° C.

EXAMPLE 2

Synthesis of cyclohexylideneacetyl(lys$_{77}$ plasmin A chain)ile$_{159}$ u-PA (CHA→u-PA hybrid)

(a) Preparation of ethyl cyclohexylideneacetate

Triethylphosphonoacetate (2.50 g, 2.21 ml) was added dropwise to a suspension of sodium hydride (80% in oil, 370 mg) in dimethoxyethane (15 ml). The solution was allowed to stir at room temperature under an atmosphere of dry nitrogen or approximately 30 min. When evolution of hydrogen had ceased, cyclohexanone (1.09 g, 1.15 ml) was added dropwise and the reaction mixture was allowed to stir for 5h, the reaction being followed by thin layer chromatography (tlc). After this time water (50 ml) was added and the aqueous layer was extracted with dichloromethane (2×50 ml). The organic layer was dried, filtered and evaporated to leave an oil. This was purified by bulb to bulb distillation (approximately 130° C. at 2 mmHg) to leave the sweet-smelling title compound (a) (1.04 g, 55%).

Nmr: δ(CDCl$_3$) 5.6 (1H, m, C=C—H̱), 4.15 (2H, q, J=7 Hz), OCH̱$_2$), 2.8 (2H, br t, —C=C—CH̱$_2$ cis to ester), 2.2 (2H, br t, —C=C—CH̱$_2$ trans to ester), 1.6 (8H, m, 4×CH̱$_2$) and 1.3 (3H, t, J=7 Hz, CH$_2$CH̱$_3$).

IR: ν$_{max}$(thin film) 2950, 2870, 1715, 1690, 1205, 1155, 1040, 850 and 610 cm$^{-1}$.

(b) Preparation of cyclohexylideneacetic acid

The ethyl ester from (a) (343 mg, 2.04 mmol) was dissolved in ethanol (5 ml). A 5M aqueous solution of sodium hydroxide (0.82 ml, 4.04 mmol) was added. The solution was stirred at reflux for 3h whereupon a precipitate was formed, and all starting material had disappeared as indicated by tlc. After cooling, the ethanol was removed by evaporation and water (10 ml) was added. The basic solution was extracted with dichloromethane (10 ml) which was discarded. The aqueous layer was acidified with 2M hydrochloric acid and then extracted with ethyl acetate (2×10 ml). The organic layer was dried, filtered and evaporated to leave the title compound (b) (206 mg, 72%) as a sweet-smelling white solid, m.p. 84°-5° C. from ethanol and diethylether.

Nmr: δ(CDCl$_3$) 12.3 (1H, s, CO$_2$H̱), 5.65 (1H, s, CH̱=C), 2.9 (2H, m, CH̱$_2$—C=C cis to acid), 2.25 (1H, m, CH̱$_2$—C=C, trans to acid), 1.65 (6H, s, 3×CH̱$_2$).

IR: ν$_{max}$ (Nujol) 2300–3400, 1680, 1640, 1420, 1310, 1275, 1260, 1225, 1185, 879 and 705 cm$^{-1}$.

Found C, 68.55; H, 8.63. C$_8$H$_{12}$O$_2$ requires C, 68.65; H, 8.56%.

(c) Preparation of 4-amidinophenyl cyclohexylideneacetate hydrochloride salt

The acid from (b) (175 mg, 1.25 mmole) was dissolved in pyridine (5 ml). 4-Amidinophenol (215 mg, 1.25 mmole) was added followed by dicyclohexylcarbodiimide (517 mg, 2.5 mmole) and 4-toluenesulphonic acid. The reaction was stirred at room temperature for 6d under an atmosphere of nitrogen after which infra red spectroscopy showed that the reaction was proceeding no further. The solution was filtered and the pyridine was removed by evaporation. The residual gum was first recrystallized from chloroform and petroleum ether (40°–60° C. and then from ethanol and diethylether to leave a white solid (134 mg, 35%), m.p. 175°–180° C.

Nmr: δ(d$^6$DMSO) 9.3 (4H, br s, NH̱$_2$), 7.95 and 7.25 (4H, AB quartet, aryl-H̱), 5.8 (1H, m, CH̱=C), 2.80 (2H, CH̱$_2$—C=C cis to ester), 2.20 (2H, CH̱$_2$—C=C trans to ester), 1.6 (6H, br, s, 3×CH̱$_2$).

IR: ν$_{max}$ (Nujol) 2800–3400, 1735, 1680, 1640, 1605, 1480, 1215, 1120, 1020, 990, 820 and 610 cm$^{-1}$.

Found C, 59.49; H, 6.56; N, 9.28. C$_{15}$H$_{19}$N$_2$O$_2$Cl.½H$_2$O requires C, 59.30; H, 6.63; N, 9.22%.

(d) Title compound

Approximately 540,000 IU* highly purified $lys_{77}$ plasmin A-chain/$ile_{159}$ u-PA (3.0 mg protein) in 1.9 ml PBS 'A' (Dulbecco)/0.01% Tween 80/0.02M ε-aminocaproic acid (EACA) was diluted with PBS 'A'/0.01% Tween 80 (0.2 ml) and 0.25M L-lysine/100 mg ml$^{-1}$ mannitol/10 mM EACA (0.24 ml). To this solution was added 5.7 μl acylating agent from (c) (10 mM in DMSO). The mixture was incubated at 25° C.; after 40 min only 3% of the original amidolytic activity remained. The mixture was buffer-exchanged into PBS 'A'/0.01% Tween 80/0.02M EACA (4.4 ml) and stored at −70° C.

An aliquot of the CHA→u-PA hybrid was later deacylated by incubating it in 9 volumes PBS 'A'/0.01% Tween 80° at 25° C. and measuring the return of amidolytic activity. The deacylation rate constant was calculated to be $2.4 \times 10^{-4}$ sec$^{-1}$, giving a deacylation half life of 47 min. The measurements confirmed that before deacylation 97 percent of the CHA→u-PA hybrid was in the acyl form.

*International Standard for t-PA, Lot 83/517

BIOLOGICAL DATA

Clearance of plasminogen activators from the bloodstream of guinea pigs

Method

Male Dunkin Hartley guinea pigs (350–470 g) were anaesthetized with urethane (25% w/v solution; 6 ml/kg i.p.). One carotid artery was cannulated for collection of blood samples. One jugular vein was cannulated for injection of heparin (100 U/Kg i.v.) and the compound under test. Approximately 5 min after heparinization, a pre-dose blood sample (1 ml) was taken and mixed with 0.1 volumes 129 mM trisodium citrate. The compound under test was then injected (0.5 nmol/kg) over 15s (1 ml/kg). Further blood samples (0.6 ml) were taken exactly 4, 8, 16, 30, 60 and 90 min later. All citrated blood samples were centrifuged as soon as available at 1700 g for 15 min at 4° C. to obtain plasma. The euglobulin fraction was immediately precipitated by adding 0.05 ml of each plasma to 0.9 ml ice-cold 0.011% (v/v) acetic acid in water. After 30 min standing in ice, all tubes were centrifuged at 1700 g for 15 min at 4° C. The supernatants were poured away, the inner walls of each tube carefully wiped dry and each precipitate redissolved in 0.5 ml phosphate-buffered saline, pH 7.4, containing 0.01% (v/v) Tween 80.

Aliquots (30 λl) were then applied to fibrin plates in quadruplicate. Fibrin plates were prepared from 0.4% (w/v) human fibrinogen (Kabi, Grade L, Flow Laboratories, Scotland) dissolved in 0.029M barbitone in 125 mM NaCl, pH 7.4 pipetted (10 ml) into 10×10 cm square plastic dishes (Sterilin) and clotted by rapid mixing with 0.3 ml bovine thrombin (50 NIH units/ml, Parke-Davis, U.K.). Plates were incubated at 37° C. for 18–24h and stained with aqueous bromophenol blue.

For each lysis zone, two diameters perpendicular to each other were measured using Vernier callipers. All diameters for each sample were averaged, and this mean converted to concentration by reference to a calibration curve obtained by adding known amounts of the compound under test to ice-cold pre-dose plasma from each animal. These standards were processed using the same methods and at the same time as the experimental samples. To construct the calibration curve, diameters (mm) were plotted against log concentration of compound. The plasma concentration of compound in each experimental sample was expressed as log percentage of the initial concentration expected (on the assumption of 37 ml plasma/kg body weight of each guinea pig) and plotted against time.

Results

The clearance pattern for 4-aminobenzoyl-u-PA (AB→u-PA) was biphasic; the initial rate of clearance was very rapid (half-life, 3 min) and accounted for 70–80% of the injected dose. The remainder disappeared with a half-life of 20 min. The clearance data for AB→u-PA hybrid fitted a straight line; dividing ln 0.5 by the slope of the line revealed a half-life of 81 min.

We claim:

1. A hybrid protein which comprises plasmin A-chain linked to urokinase B-chain, the catalytic site of which is blocked by a removable blocking group.

2. A hybrid protein according to claim 1, wherein the removable blocking group is removable by hydrolysis at a rate such that the pseudo-first order rate constant for hydrolysis is in the range of $10^{-6}$ sec$^{-1}$ to $10^{-2}$ sec$^{-1}$ in isotonic aqueous media at pH 7.4 at 37° C.

3. A hybrid protein according to claim 2, wherein the removable blocking group is an acyl group.

4. A hybrid protein according to claim 3, wherein the group is optionally substituted benzoyl or optionally substituted acryloyl.

5. A hybrid protein according to claim 4, wherein the acyl group is benzoyl optionally substituted by halogen, $C_{1-6}$ alkyl, $C_{1-6}$ alkoxy, $C_{1-6}$ alkanoyloxy, $C_{1-6}$ alkanoylamino, amino or p-guanidino, or acryloyl optionally substituted by $C_{1-6}$ alkyl, furyl, phenyl or $C_{1-6}$ alkylphenyl, or disubstituted by $C_{3-6}$ polymethylene.

6. A hybrid protein according to claim 5, wherein the removable blocking group is 4-aminobenzoyl or cyclohexylideneacetyl.

7. 4-Aminobenzoyl ($lys_{77}$ plasmin A-chain)$ile_{159}$ u-PA or cyclohexylideneacetyl($lys_{77}$ plasmin A chain)$ile_{159}$ u-PA.

8. A pharmaceutical composition comprising a hybrid protein according to claim 1 in which combination with a pharmaceutically acceptable carrier.

9. A method of treating thrombotic diseases, which comprises administering to the sufferer an effective non-toxic amount of a hybrid protein according to claim 1.

* * * * *